US00PP32907P2

(12) United States Plant Patent
Rodriguez Mesa

(10) Patent No.: US PP32,907 P2
(45) Date of Patent: Mar. 23, 2021

(54) BLACKBERRY PLANT NAMED 'EXPB3181'

(50) Latin Name: ***Rubus subgenus Eubatus* sect. Moriferi & Ursini**
Varietal Denomination: EXPB3181

(71) Applicant: Expoberries, S.A. de C.V., Los Reyes (MX)

(72) Inventor: Jose Maurilio Rodriguez Mesa, Los Reyes (MX)

(73) Assignee: Expoberries, S.A. de C.V., Los Reyes (MX)

( * ) Notice: Subject to any disclaimer, the term of this patent is extended or adjusted under 35 U.S.C. 154(b) by 0 days.

(21) Appl. No.: 16/602,486

(22) Filed: Oct. 17, 2019

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203, 204
See application file for complete search history.

*Primary Examiner* — Susan McCormick Ewoldt
(74) *Attorney, Agent, or Firm* — Jimmy Zhou

(57) ABSTRACT

The present invention is a new and distinct primocane fruiting blackberry variety designated 'EXPB3181'. This new variety was discovered after planting a seed produced by a hand pollinated cross of 'Kiowa' (U.S. Plant Pat. No. 9,861) and selection 'SP709' (non-patented) in Los Reyes, Michoacan, Mexico. The new variety exhibits excellent fruit quality, erect plant habit and minimal thorns. The new variety is also recognized for ripening early and having a long shelf life.

5 Drawing Sheets

Latin name of the genus and species: *Rubus* subgenus *Eubatus* sect. Moriferi & Ursini.
Variety denomination: 'EXPB3181'.

BACKGROUND OF THE NEW VARIETY

The present invention relates to a new and distinct variety of blackberry having the denomination 'EXPB3181'. This new cultivar was created in 2013 in Los Reyes, Michoacan, Mexico and originated from a hand pollination cross of the female parent blackberry plant 'Kiowa' (U.S. Plant Pat. No. 9,861) and the male parent blackberry plant selection 'SP709' (non-patented). The botanical designation of the new variety of blackberry is *Rubus* subgenus *Eubatus* sect. Moriferi & Ursini.

Seeds originating from this controlled hand pollination cross were germinated in a greenhouse in 2013 and planted in a field in Los Reyes, Michoacan, Mexico. The seedlings fruited in the autumn of 2014 and one seedling, designated 'EXPB3181', was selected for propagation for its excellent fruit quality, erect habit and minimal thorns.

The selected plant was propagated asexually from root cuttings in 2014 in Los Reyes, Michoacan, Mexico. There, a test row of 50 plants was established. Larger test fields were later established and the cultivar was further asexually reproduced in Zacoalco de Torres, Jalisco, Mexico at nursery Teocuitatlán De Corona using root cuttings from the Los Reyes test site.

The new variety has been asexually multiplied annually since 2014 by use of root cuttings and by tissue culture. During all asexual multiplication, the characteristics of the original plant have been found to be stable and no aberrant phenotypes have appeared. Testing has confirmed that the characteristics of the new variety are fixed and retained true to type through successive generations.

SUMMARY OF THE NEW VARIETY

The present invention is a new and distinct primocane fruiting blackberry variety designated 'EXPB3181'. This new variety was discovered after planting a seed produced by a hand pollinated cross of 'Kiowa' (U.S. Plant Pat. No. 9,861) and selection 'SP709' (non-patented) in Los Reyes, Michoacan, Mexico. The new variety exhibits excellent fruit quality, erect plant habit and minimal thorns. The new variety is also recognized for ripening early and having a long shelf life.

BRIEF DESCRIPTION OF THE PHOTOGRAPHS

The accompanying photographs show typical characteristics of the new variety. The plants depicted in the photographs were grown in Zacoalco de Tones, Jalisco, Mexico.

DETAILED BOTANICAL DESCRIPTION

Figure 1:
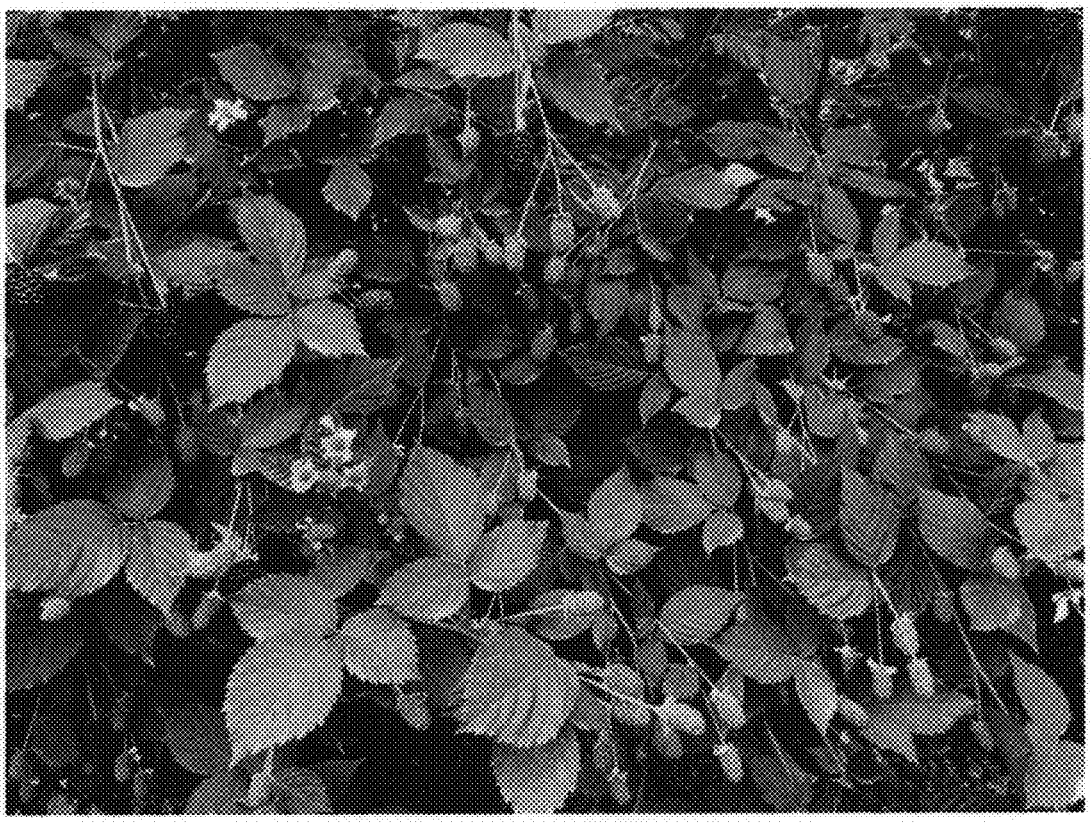
FIG. 1 shows several three-year-old plants of the new variety with several fruits in different stages of ripening.
Figure 2:
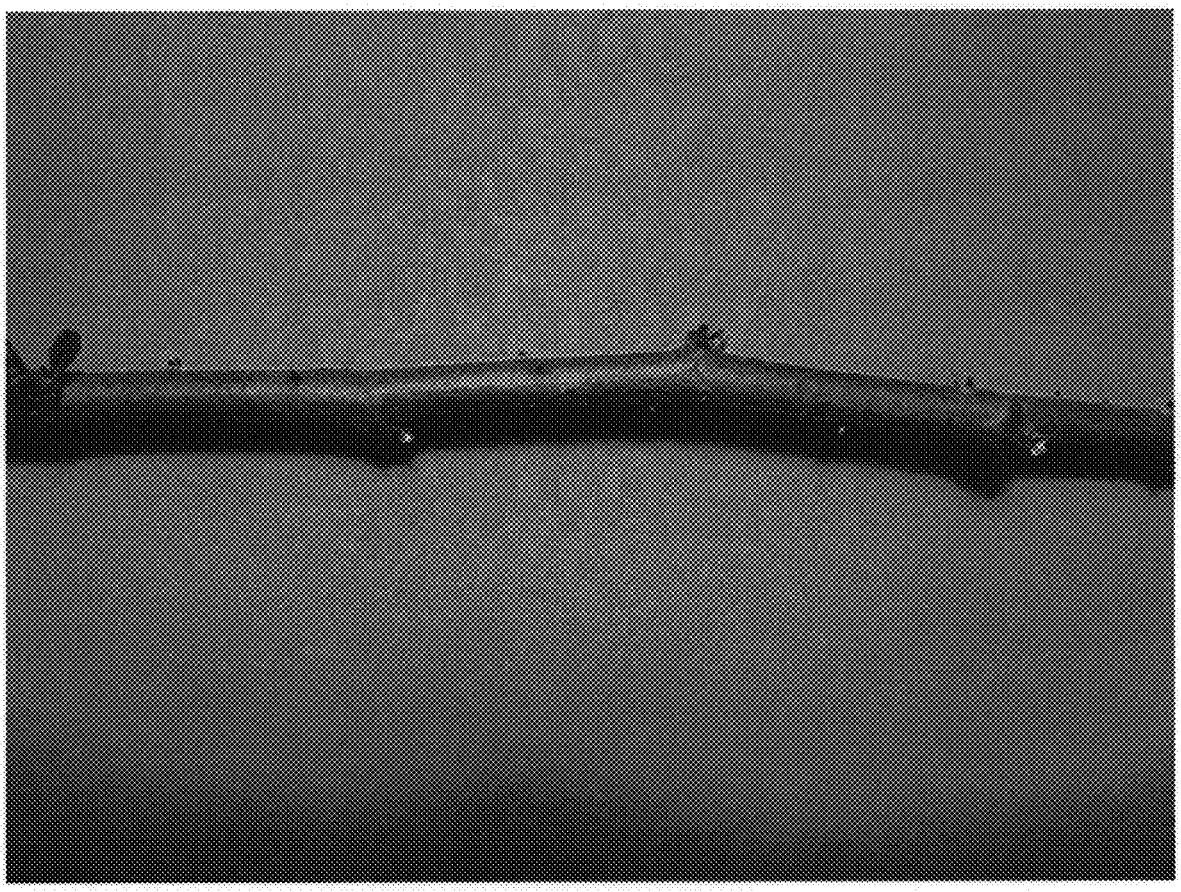
FIG. 2 shows the cane of the new variety with RHS moderate green yellow color (138 B Green group).
Figure 3:
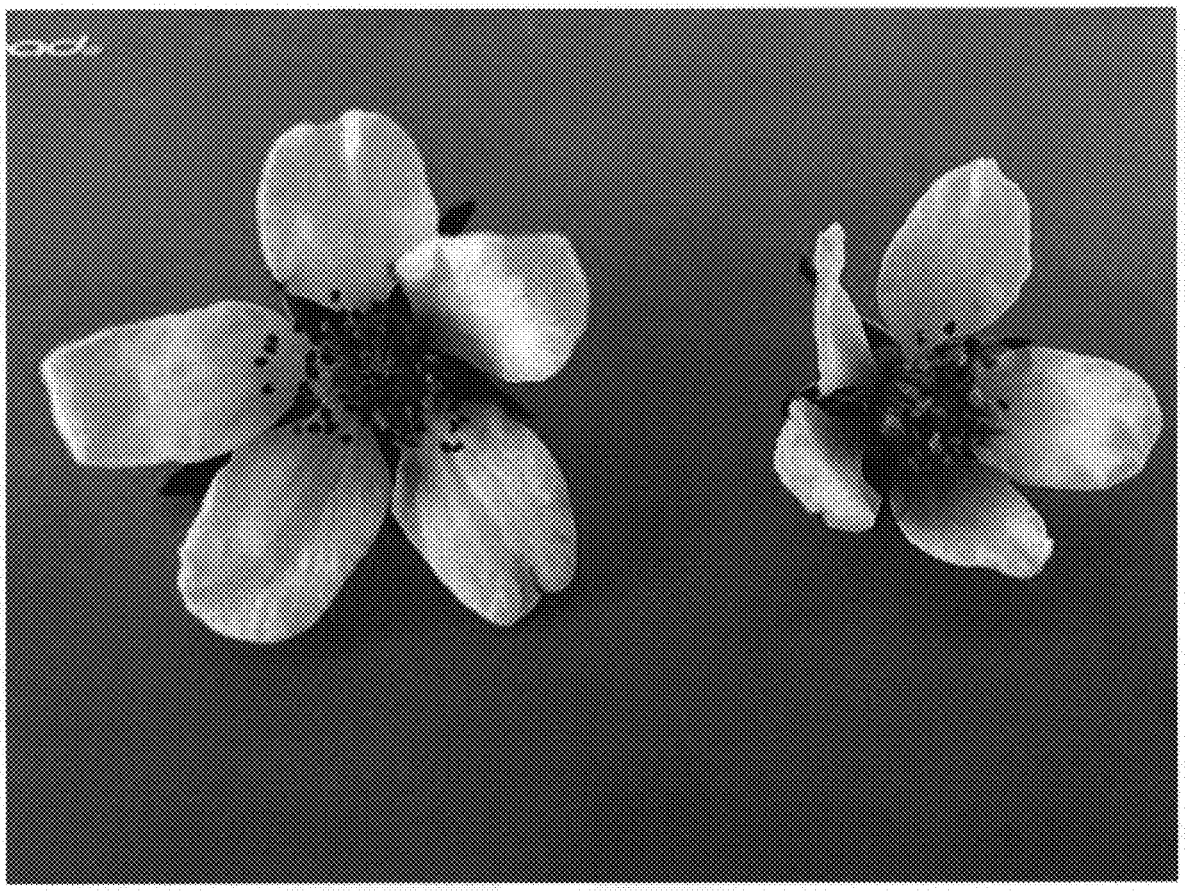
FIG. 3 shows typical flowers of the new variety having petals with RHS very pale purple color (near 76 D).
Figure 4:
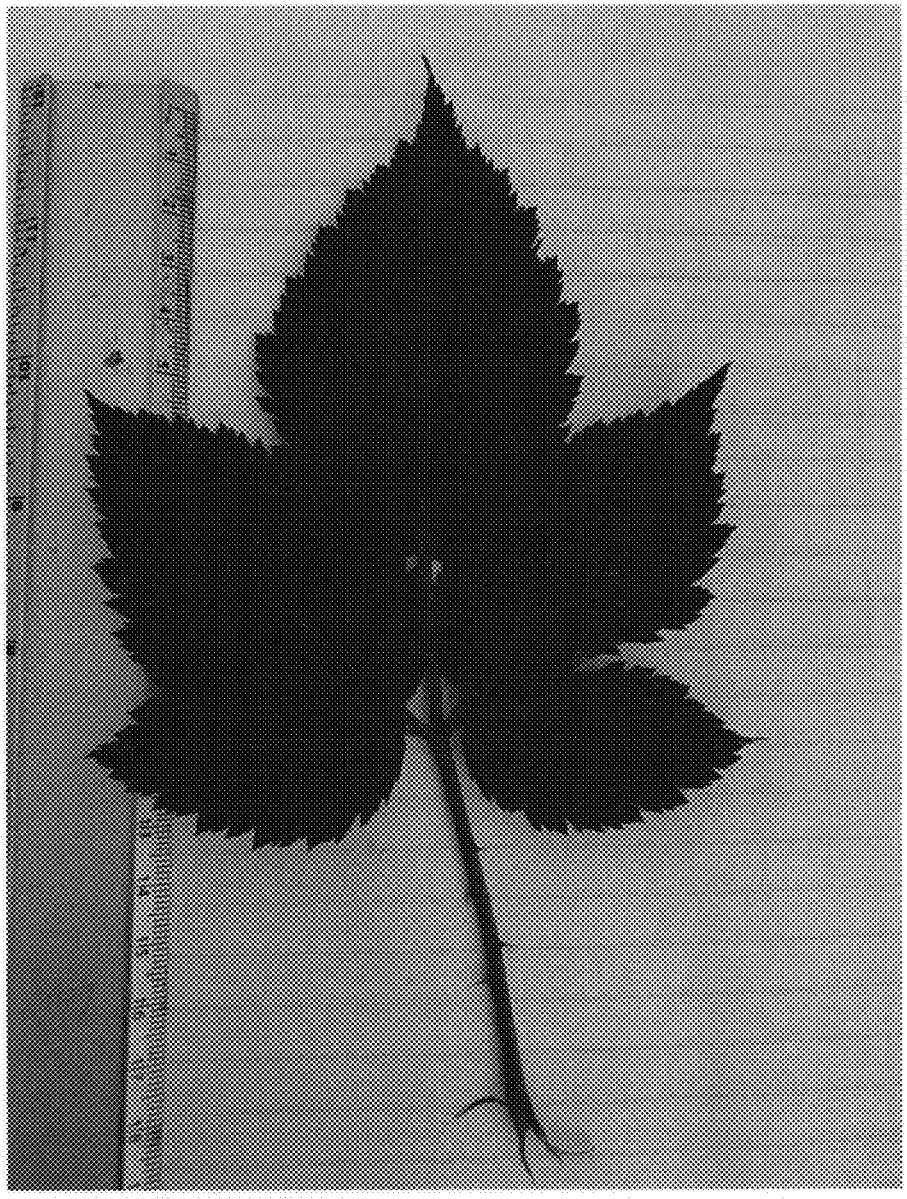
FIG. 4 shows the upper surface of a mature compound leaf of the new variety with RHS moderate Olive Green color (near 147 A).
Figure 5:
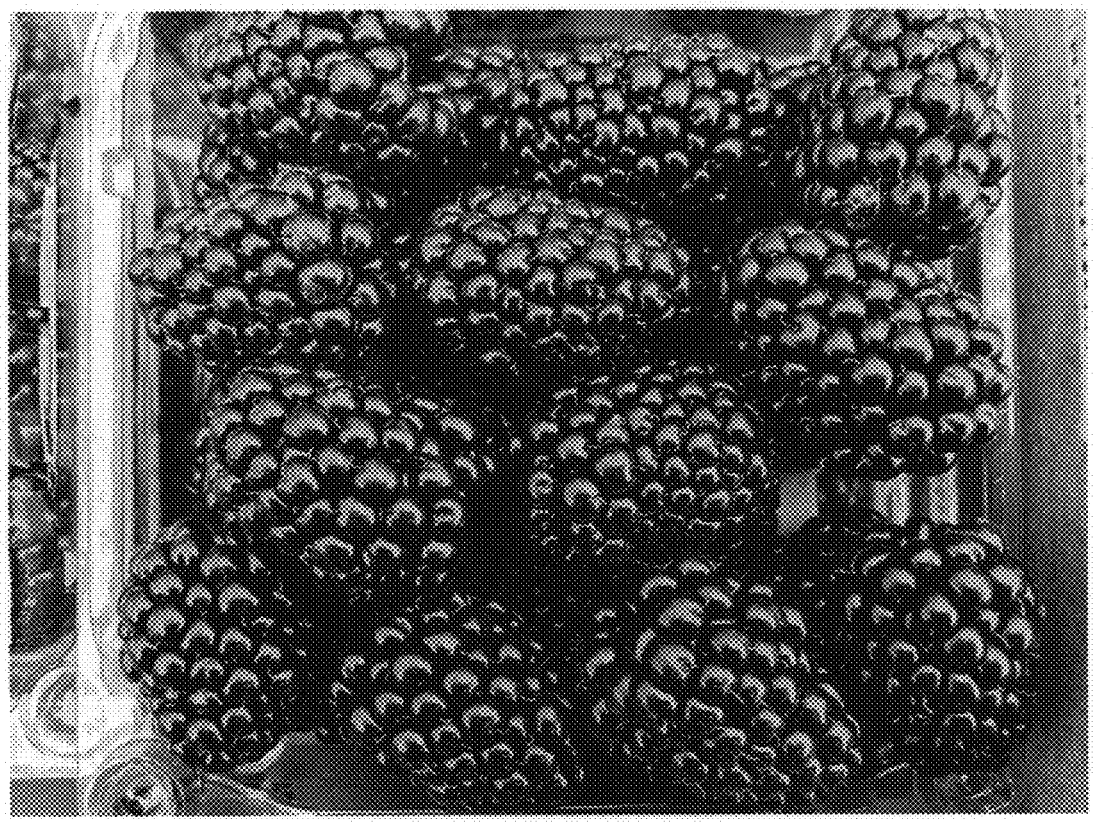
FIG. 5 shows typical fruits of the new variety having an ovate shape, strong glossiness, and RHS Black group color (near 203 C).

The following is a detailed description of the new and distinct variety, designated 'EXPB3181', including fruit production, together with the variety's morphological characteristics. Unless indicated otherwise, color references are made to R.H.S. Colour Chart of The Royal Horticultural Society of London, 6th edition, 2015.

The new variety resulted from a hand pollination cross of 'Kiowa' (U.S. Plant Pat. No. 9,861) and selection 'SP709'

(non-patented). Germinating seeds were planted in a trial row of 50 plants in a field in Los Reyes, Michoacan, Mexico. After successful trials, a larger testing site was established in Zacoalco de Torres, Jalisco, Mexico. The seedlings fruited in Autumn 2014 and one plant of the new varietal was selected for propagation. The new variety was selected for its excellent fruit quality, erect habit and minimal thorns.

The new variety was propagated asexually from root cuttings in 2014. The new variety has been asexually multiplied annually since 2014 by use of root cuttings and by tissue culture. During all asexual multiplication, the characteristics of the original plant have been found to be stable and no aberrant phenotypes have appeared. Testing has confirmed that the characteristics of the new variety are fixed and retained true to type through successive generations.

The new variety is a primocane variety with fruit production peaking in October through December. The growing period is between May 15 to April 30 of the following year. Planting begins around May. The variety begins to flower around September. Plants are grown in raised beds under high tunnels. Fertilizer is provided through drip irrigation. The new variety has demonstrated resistance to leaf rust. While propagation by root cuttings is preferred, other known methods of propagating blackberry plants may be used. Blackberries root and develop well after transplanting.

The following information is in accordance with UPOV terminology and the color terminology herein is in accordance with The R.H.S. Colour Chart of The Royal Horticultural Society of London. The color descriptions and other phenotypical descriptions may deviate from the stated values and descriptions depending upon variation in environmental, seasonal and climatic conditions. Where dimensions, sizes, colors, and other characteristics are given, it is to be understood that such characteristics are approximations of averages set forth as accurately as practicable. Observations were made on the plants grown in Zacoalco de Torres, Jalisco, Mexico. The plants are observed and described during their primocane.

Classification:

*Family*.—Rosaceae.

*Botanical taxon*.—*Rubus* subgenus *Eubatus* sect. Moriferi & Ursini.

*Common name*.—Blackberry.

*Variety name*.—'EXPB3181'.

Plant:

*Vigor*.—Medium.

*Growth habit*.—Semi-upright.

*Productivity*.—Medium.

*Propagation*.—Tissue culture and root cuttings.

*Self-fruitfulness*.—Self-fertile.

*Length* (*free growth*).—280 to 300 cm (average of 290 cm).

*Length* (*commercial hedge*).—average of 170 cm.

*Width* (*free growth*).—average of 120 cm.

*Width* (*commercial hedge*).—average of 90 cm.

Primocane (mature):

*Diameter*.—At base: 8.0 mm. At midpoint: 6.0 mm. At terminus: 4.5 mm.

*Internode length*.—At base: 6.0 cm. At midpoint: 4.0 cm. At terminus: 3.0 cm.

*Thorn density* (*per* 30 *cm of cane length*).—At base: 33. At midpoint: 15. At terminus: 12.

*Color*.—At base: RHS 138A. At midpoint: RHS 138B. At terminus: RHS 138B.

Cane color: RHS strong yellow green, near 145A.

Fruiting:

*Lateral length*.—Medium.

*Length average*.—40 cm.

*Width*.—3 to 5 mm.

*Number of fruit per lateral*.—9 to 11.

Shoot:

*Number of young shoots*.—8 to 12 per plant.

*Very young shoots intensity of anthocyanin coloration*.—Absent or very weak.

*Time of young shoot emergence from soil*.—March (Mexico).

*Young shoot pigmentation*.—RHS 143A (strong yellow green).

*Shoot length*.—160 to 240 cm.

*Glaucosity*.—Present on mature canes.

*Cane cross section*.—Rounded.

*Dormant cane color*.—RHS 138A (moderate yellow green).

*Pubescence on canes*.—Present (very small).

Cane internodal distance:

*Internodal distance at central third of cane*.—4 to 6 cm (average of 5 cm).

Leaves:

*Mature compound leaf length*.—22 cm.

*Mature compound leaf width*.—17.5 cm.

*Color*.—Adaxial: RHS 147A (moderate olive green). Abaxial: RHS 138A (moderate green).

*Arrangement*.—Palmate.

*Number of leaflets*.—5.

*Relief between veins*.—Medium.

*Glossiness*.—Weak.

*Cross section profile*.—V-shape.

*Petiole*.—Length: 4 to 6 cm (average of 5 cm). Color: RHS 141B (deep yellow green). Diameter: average of 2.0 mm.

*Petiolule*.—Length: 1.2 cm. Color: RHS 141B (deep yellow green). Diameter: average of 1.0 mm.

*Terminal leaflet*.—Length: average of 11.0 cm. Width: average of 7 cm. Color (upper surface): RHS 147A (moderate olive green). Color (lower surface): RHS 147B (moderate yellow green). Margin: Biserrate. Shape of leaflet: Ovate. Shape of base: Cordate. Shape of apex: Cuspidate. Teeth length: 2.0 mm. Teeth width: 1.0 mm.

*Stipule*.—Absent or very small.

Inflorescence:

*Type*.—Elongated simple cyme.

*Time of flowering*.—September to November.

*Number of flowers per cluster*.—3.

*Flower diameter*.—Average of 4 cm.

*Flower depth*.—Average of 1.0 cm.

*Flower disc diameter*.—Average of 0.6 cm.

*Diameter of calyx relative to corolla*.—2.0 cm.

*Flower number* (*at* 3*rd node from tip of lateral*).—6 to 9 flowers per cluster.

*Petal*.—Length: average of 2.0 cm. Width: average of 1.0 cm. Color: RHS 76D (very pale purple).

*Sepal*.—Length: average of 1.5 cm. Width: average of 0.5 cm. Shape: Triangular. Color: RHS 135C (strong yellow green).

*Peduncle*.—Length: 2.2 cm. Diameter: 0.2 cm. Color: RHS 147C.

*Pedicel*.—Length: 1.2 cm. Diameter: 0.1 cm. Color: RHS 147C.

Fruit:

*Time of ripening*.—Early (pursuant to UPOV TG/73/7 for *Rubus*, subgenus *Eubatus* sect. Moriferi & Ursini).

*Harvest interval*.—November to January.

*Length of harvest season*.—8 to 10 weeks.

*Color at maturity*.—RHS 203C (black).

*Glossiness*.—Strong.

*Shape*.—Medium ovate.

*Length*.—2.5 to 3.5 cm (average of 3.0 cm).

*Width*.—1.8 to 2.2 cm (average of 2.0 cm).

*Ratio of length to width*.—1.5:1.0 cm.

*Weight* (*g/fruit*).—Average of 8.0 g.

*Soluble solids* (%) (*in Brix*).—18%.

*Number of druplets/fruit*.—80.

*Firmness*.—Very firm.

*Yield*.—1.5 kg/fruit/plant.

The characteristics of this new cultivar are phenotypically distinguishable from the characteristics of its parents, 'Kiowa' (U.S. Plant Pat. No. 9,861) and selection 'SP709' (non-patented). The fruit of the new cultivar ripens earlier and possesses better firmness and better flavor than the fruit of 'Kiowa' (U.S. Plant Pat. No. 9,861). Additionally, the plant of the new cultivar is less vigorous and less productive than the plant of 'Kiowa' (U.S. Plant Pat. No. 9,861). The fruit of the new cultivar is smaller than the fruit of 'Kiowa' (U.S. Plant Pat. No. 9,861) and selection 'SP709' (non-patented). The fruit of the new cultivar also ripens earlier than the fruit of selection 'SP709' (non-patented). Further, the plant of the new cultivar is more productive than the plant of selection 'SP709' (non-patented). The shelf life for the fruit of the new cultivar is better than that of either of its parents, 'Kiowa' (U.S. Plant Pat. No. 9,861) and selection 'SP709' (non-patented). The new cultivar maintains the ripen fruit in good condition on the plant for three to four days longer than the fruit of 'Kiowa' (U.S. Plant Pat. No. 9,861) or selection 'SP709' (non-patented).

'EXPB3181' has not been observed under all possible environmental conditions and as such the characteristics may vary in detail depending on weather conditions, day length, soil type and location. The blackberries of 'EXPB3181' are suitable for consumption as fresh fruit.

What is claimed:

1. A new and distinct blackberry plant known as 'EXPB3181' as described herein, illustrated and identified by the characteristics set forth above.

* * * * *